United States Patent
Balczewski et al.

(10) Patent No.: US 11,253,710 B2
(45) Date of Patent: Feb. 22, 2022

(54) CHIP OR SILICON BASED FEEDTHROUGH

(71) Applicant: Cardiac Pacemakers, Inc., St. Paul, MN (US)

(72) Inventors: Ron A. Balczewski, Bloomington, MN (US); James E. Blood, Shoreview, MN (US); William J. Linder, Golden Valley, MN (US); Jacob M. Ludwig, Isanti, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 547 days.

(21) Appl. No.: 15/863,177

(22) Filed: Jan. 5, 2018

(65) Prior Publication Data

US 2018/0185655 A1    Jul. 5, 2018

Related U.S. Application Data

(60) Provisional application No. 62/442,786, filed on Jan. 5, 2017.

(51) Int. Cl.
*A61N 1/37* (2006.01)
*A61N 1/375* (2006.01)
(Continued)

(52) U.S. Cl.
CPC ............ *A61N 1/3754* (2013.01); *A61N 1/05* (2013.01); *A61N 1/3758* (2013.01); *A61N 1/37512* (2017.08); *A61N 1/3956* (2013.01)

(58) Field of Classification Search
CPC .... A61N 1/05; A61N 1/37512; A61N 1/3754; A61N 1/3956
See application file for complete search history.

(56) References Cited

U.S. PATENT DOCUMENTS

2008/0312726 A1* 12/2008 Frank ............... A61N 1/375
607/122
2009/0163981 A1    6/2009 Stevenson et al.
(Continued)

FOREIGN PATENT DOCUMENTS

| CN | 110167633 A | 8/2019 |
|---|---|---|
| WO | WO-2014049089 A1 | 4/2014 |

OTHER PUBLICATIONS

"European Application Serial No. 18701841.1, Response to Communication Pursuant to Rules 161 and 162 EPC filed Mar. 5, 2020", left electronic receipt in PDF because response was drafted Mar. 3, 2020 but it was filed with EPO dated Mar. 5, 2020, 12 pgs.

(Continued)

*Primary Examiner* — Amanda K Hulbert
(74) *Attorney, Agent, or Firm* — Schwegman Lundberg & Woessner, P.A.

(57) ABSTRACT

This document discusses, among other things, systems and methods to fabricate and operate an implantable medical device. The implantable medical device can include a housing portion defining an interior chamber. The implantable medical device can include a circuit in the interior chamber. The implantable medical device can include a first electronic component that is not in the interior chamber. The implantable medical device can include a substrate coupled to the housing, the substrate including a first via extending through the substrate, the first via electrically coupling the first electronic component to the circuit.

18 Claims, 7 Drawing Sheets

(51) Int. Cl.
*A61N 1/39* (2006.01)
*A61N 1/05* (2006.01)

(56) References Cited

U.S. PATENT DOCUMENTS

| | | | |
|---|---|---|---|
| 2009/0259265 A1 | 10/2009 | Stevenson et al. | |
| 2009/0321107 A1* | 12/2009 | Taylor | H01M 2/08 |
| | | | 174/11 OR |
| 2015/0157862 A1* | 6/2015 | Greenberg | H05K 1/11 |
| | | | 607/60 |

OTHER PUBLICATIONS

"International Application Serial No. PCT/US2018/012470, International Preliminary Report on Patentability dated Jul. 18, 2019", 7 pgs.
"International Application Serial No. PCT/US2018/012470, International Search Report dated Mar. 27, 2018", 5 pgs.
"International Application Serial No. PCT/US2018/012470, Written Opinion dated Mar. 27, 2018", 5 pgs.
Chan, Ho-Yin, "Polycrystalline Cvd Diamond Probes for Use in In Vivo and In Vitro Neural Studies", A dissertation submitted to Michigan State University, 2008, 137 pages, https://www.egr.msu.edu/~aslam/NeuralProbeDiam_ChanH_thesis_08.pdf.

* cited by examiner

CHIP OR SILICON BASED FEEDTHROUGH

CLAIM OF PRIORITY

This application claims the benefit of priority under 35 U.S.C. § 119(e) of U.S. Provisional Patent Application Ser. No. 62/442,786, filed on Jan. 5, 2017, which is herein incorporated by reference in its entirety.

TECHNICAL FIELD

This document relates generally to medical devices, and more particularly, but not by way of limitation, to systems, devices, and methods to transmit electrical signals to the exterior of a medical device.

BACKGROUND

Implantable medical devices, such as cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions. To alleviate one or more of these conditions, various medical devices can be implanted in a patient's body to monitor heart activity or to provide electrical stimulation to optimize or control contractions of the heart.

For example, a cardiac rhythm management (CRM) device, such as a pacemakers or defibrillator, can be implanted in a patient. Some CRM devices can be connected to one or more leads to position one or more electrodes or other sensors at various locations in or around the heart, such as in or on one or more of the atria or ventricles.

SUMMARY

This document discusses, among other things, systems and methods to provide a feedthrough for an implantable medical device.

An example (e.g., "Example 1") of subject matter (e.g., a system) may include a housing portion defining an interior chamber, a circuit in the interior chamber, a first electronic component that is not in the interior chamber, a substrate coupled to the housing, the substrate including a first via extending through the substrate, the first via electrically coupling the first electronic component to the circuit.

In Example 2, the subject matter of Example 1 may optionally be configured such that the housing includes portions that define an opening, and the substrate is hermetically coupled to the housing proximate the opening.

In Example 3, the subject matter of any one or more of Examples 1-2 may optionally be configured such the implantable medical device includes a micro-electromechanical system ("MEMS") that includes the first electronic component.

In Example 4, the subject matter of any one or more of Examples 1-3 may optionally be configured such that the micro-electromechanical system includes a pressure sensor.

In Example 5, the subject matter of any one or more of Examples 1-4 may optionally be configured such that the first electronic component is integrated onto the substrate In Example 6, the subject matter of any one or more of Examples 1-5 may optionally be configured such that the opening in the housing portion has a first set of rounded corners and the substrate includes a second set of rounded corners that match the first set of rounded corners to facilitate hermetically sealing the implantable medical device feedthrough to the housing.

In Example 7, the subject matter of any one or more of Examples 1-6 may optionally be configured to include a plurality of electrodes that includes the first electronic component.

In Example 8, the subject matter of any one or more of Examples 1-7 may optionally be configured to include circuitry that is configured to activate a selected subset of the plurality of electrodes.

In Example 9, the subject matter of any one or more of Examples 1-8 may optionally be configured such that the first electronic component is a spike electrode and the spike electrode has one or more isolated sub-electrodes.

In Example 10, the subject matter of any one or more of Examples 1-9 may optionally be configured such that the substrate is made from the class of materials known as semiconductors.

In Example 11, the subject matter of any one or more of Examples 1-10 may optionally be configured such that In Example 12, the subject matter of any one or more of Examples 1-11 may optionally be configured to include a plurality of electronic components that includes the first electronic component, and also includes an array of sensors.

In Example 13, the subject matter of any one or more of Examples 1-12 may optionally be configured to include a plurality of electronic components that includes the first electronic component, and also includes a plurality of stimulation electrodes.

In Example 14, the subject matter of any one or more of Examples 1-13 may optionally be configured to include a plurality of electronic components, that includes the first electronic component, wherein the implantable medical device includes a control circuit that is configured to selectively activate a subset of the plurality of electronic components, the subset forming a selectable sensor array or a selectable stimulation array.

An example (e.g., "Example 15") of subject matter (e.g., an apparatus) may include a substrate having a first substrate surface, a second substrate surface, and one or more substrate openings extending from the first substrate surface to the second substrate surface, the first substrate surface configured for juxtaposition against a biological fluid; one or more electrically isolated vias, wherein: the vias include conductors passing through the one or more substrate openings, the conductors capable of transmitting electrical energy, and the vias are hermetically coupled to the substrate, wherein the biological fluid cannot pass through the one or more substrate openings from the first substrate surface to the second substrate surface; one or more electronic components coupled to the conductors and the first substrate surface; and one or more interconnects coupled to the conductors and the second substrate surface, wherein the one or more interconnects are in electrical communication with the one or more electronic components.

In Example 16, the subject matter of Examples 1 through 15 may optionally be configured to include one or more wells or trenches to increase the surface area of the first substrate surface that is in contact with the biological fluids.

An example (e.g., "Example 17") of subject matter (e.g., a system) may include a housing portion defining an interior chamber, the housing having portions defining an opening; a circuit in the interior chamber; a first electronic component that is not in the interior chamber; a substrate hermetically coupled to the housing proximate the opening, the substrate including a first via extending through the substrate, the first via electrically coupling the first electronic component to the circuit.

In Example 18, the subject matter Examples 17 may optionally be configured such that the implantable medical device includes a micro-electromechanical system ("MEMS") that includes the first electronic component.

In Example 19, the subject matter of any one or more of Examples 17-18 may optionally be configured such that the micro-electromechanical system includes a pressure sensor.

In Example 20, the subject matter of any one or more of Examples 17-19 may optionally be configured such that the first electronic component is integrated onto the substrate.

In Example 21, the subject matter of any one or more of Examples 17-20 may optionally be configured such that a first surface of the substrate is inside the housing and a second surface of the substrate faces outside of the housing, the via providing an electrical feedthrough that extends from the first surface to the second surface, and the first surface or the second surface is hermetically sealed against the housing.

In Example 22, the subject matter of any one or more of Examples 17-21 may optionally be configured such that the first surface of the substrate is hermetically sealed against an outer surface of the housing.

In Example 23, the subject matter of any one or more of Examples 17-22 may optionally be configured such that the opening in the housing portion has a first set of rounded corners and the substrate includes a second set of rounded corners that match the first set of rounded corners to facilitate hermetically sealing the implantable medical device feedthrough to the housing.

In Example 24, the subject matter of any one or more of Examples 17-23 may optionally be configured to include a plurality of electrodes that includes the first electronic component.

In Example 25, the subject matter of any one or more of Examples 17-24 may optionally be configured to include circuitry that is configured to activate a selected subset of the plurality of electrodes.

In Example 26, the subject matter of any one or more of Examples 17-25 may optionally be configured such that the first electronic component is a spike electrode and the spike electrode has one or more isolated sub-electrodes.

In Example 27, the subject matter of any one or more of Examples 17-26 may optionally be configured such that the substrate is made from the class of materials known as semiconductors.

An example (e.g., "Example 28") of subject matter (e.g., a system) may include a housing defining an interior chamber; one or more circuits in the interior chamber; a plurality of electronic components that are not in the interior chamber; a substrate that is configured to hermetically couple with the housing, the substrate including a plurality of vias extending through the substrate, each of the plurality of electronic components is electrically coupled to at least one of the one or more circuits through at least one of the one or more vias.

In Example 29, the subject matter Example 28 may optionally be configured such that the plurality of electronic components includes an array of sensors.

In Example 30, the subject matter of any one or more of Examples 28-29 may optionally be configured such that the plurality of electronic components includes a plurality of stimulation electrodes.

In Example 31, the subject matter of any one or more of Examples 28-30 may optionally be configured such that the implantable medical device includes a control circuit that is configured to selectively activate a subset of the plurality of electronic components, the subset forming a selectable sensor array or a selectable stimulation array.

In Example 32, the subject matter of any one or more of Examples 28-31 may optionally be configured such that wherein the plurality of electronic components form a spike electrode and the spike electrode is configured to penetrate bodily tissue.

An example (e.g., "Example 33") of subject matter (e.g., an apparatus) may include a substrate having a first substrate surface, a second substrate surface, and one or more substrate openings extending from the first substrate surface to the second substrate surface, the first substrate surface configured for juxtaposition against a biological fluid; one or more electrically isolated vias, wherein: the vias include conductors passing through the substrate openings, the conductors capable of transmitting electrical energy, and the vias are hermetically coupled to the substrate, wherein the biological fluid cannot pass through the openings from the first substrate surface to the second substrate surface; one or more electronic components electrically coupled to the conductors and the first substrate surface; and one or more interconnects coupled to the conductors and the second substrate surface, wherein the one or more interconnects are in electrical communication with the one or more electrical components.

In Example 34, the subject matter Example 1-28 may optionally be configured such that one or more wells or trenches to increase the surface area of the first substrate surface that is in contact with the biological fluids.

In Example 35, the subject matter of any one or more of Examples 33-34 may optionally be configured such that the substrate includes an elongated portion configured to penetrate bodily tissue, and further includes a base portion that includes the vias.

In Example 36, the subject matter of any one or more of Examples 33-35 may optionally be configured such that the implantable medical device feedthrough is configured to hermetically seal with a medical device housing.

An example (e.g., "Example 37") of subject matter (e.g., a system or apparatus) may optionally combine any portion or combination of any portion of any one or more of Examples 1-36 to include "means for" performing any portion of any one or more of the functions or methods of Examples 1-36, or a "machine-readable medium" (e.g., massed, non-transitory, etc.) including instructions that, when performed by a machine, cause the machine to perform any portion of any one or more of the functions or methods of Examples 1-36.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
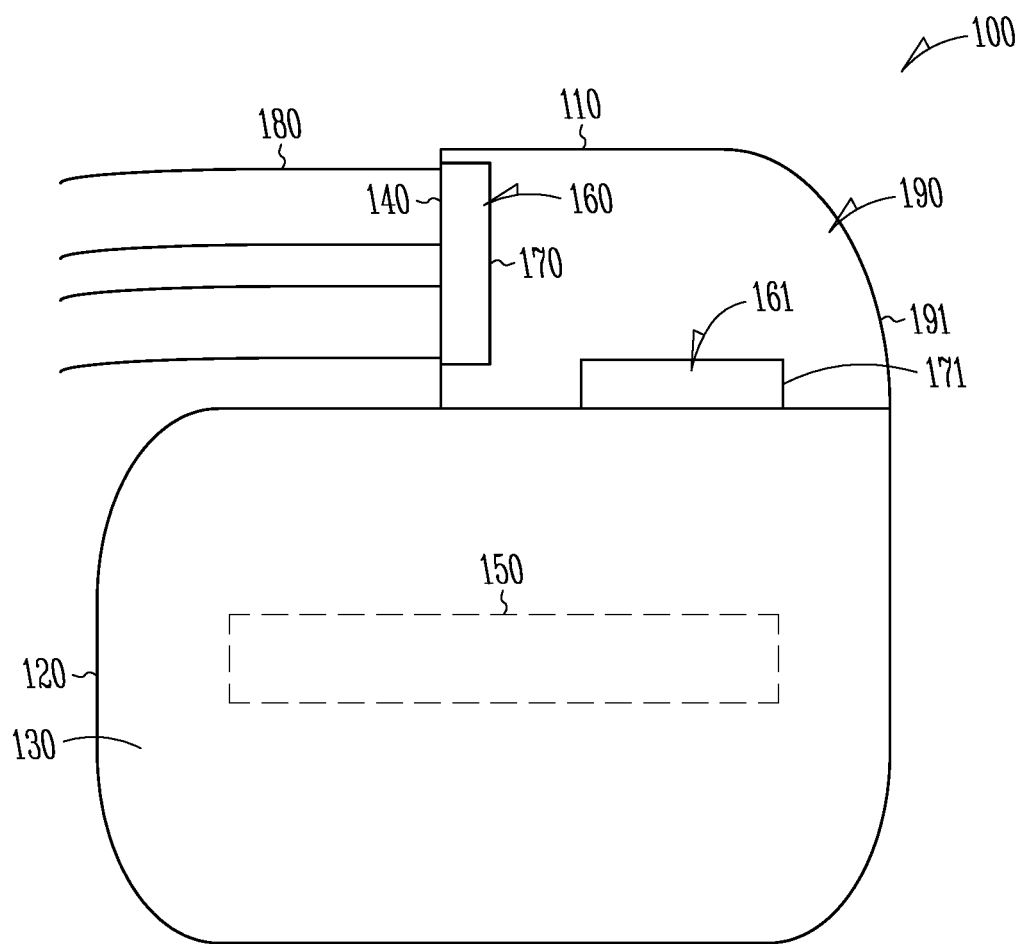
FIG. 1 illustrates an example system including an implantable medical device.

Clinically, a person may require a medical device (e.g., an implantable medical device) to be implanted within their body to address a medical condition. For example, a pacemaker can be implanted to provide pacing stimulation to the heart. An implantable cardiac resynchronization therapy (CRT) device can deliver pacing pulses to two or more chambers (e.g. left and right ventricle) to synchronize the chambers of the heart. An implantable defibrillator can be implanted to monitor for arrhythmia and, when certain conditions are detected, provide defibrillation therapy. In another example, a neurostimulator can provide stimulation to one or more regions of a person's nervous system (e.g. vagus nerve or spinal cord) or to the brain. Implantable medical devices range in size and function, and can be utilized in numerous other portions of the body. Implantable medical devices typically include a hermetically sealed housing and component such as circuits, a battery, capacitors, or other electronics that reside inside the housing.

A feedthrough formed from a substrate can be coupled to an implantable device housing and electrically coupled to circuitry in the housing to allow for electrical communication between circuitry that is located inside the housing of an implantable medical device to communicate with electronic components outside the housing of the implantable medical device (e.g., pacing or defibrillation leads, stimulation leads or electrodes, sensors, or the like).

The present inventors have recognized, among other things, that a feedthrough for an implantable medical device can be fabricated from a substrate. For example, a substrate-based feedthrough can be formed from silicon and a dielectric using chip fabrication techniques. Such a substrate-based feedthrough can be formed with one or more electrical communication pathways that allow for one or more electrically-isolated circuits to be established with external electronic components. The external electronic components can, for example be active (e.g., provide stimulation) or passive (e.g., sense physiologic signals). In an example, a substrate-based feedthrough can be hermetically sealed (e.g., coupled or otherwise connected) with the housing of the implantable medical device to prevent bodily fluids or other foreign matter from entering the housing of the implantable medical device by, for example, bonding or mechanically coupling (or both) the substrate to cover a hole in the housing. In some examples, when hermetically sealed to the housing, the feedthrough can be considered part of the housing, in the sense that the feedthrough can enclose and seal off the components inside the housing.

An implantable medical device can be fabricated from an appropriate substrate, such as silicon. The feedthrough made of an appropriate substrate can provide one or more electrically-isolated electrical communication pathways for establishing an electrical connection to one or more electronic components. In some examples, the substrate can be formed with one or more vias to passing through the substrate that can act as a feedthrough conductor. The via (e.g., trans-feedthrough conductor) can connect circuitry that is located within the housing of the implantable medical device with electronic components located outside of the housing of the implantable medical device.

The use of an appropriate substrate (e.g., silicon) for the feedthrough can allow for additional circuitry to be fabricated onto the substrate to increase the functionality of the feedthrough, such as by using integrated circuit techniques to fabricate active circuitry or sensors onto the feedthrough. The use of silicon as a substrate for the feedthrough can allow for very small electrode geometries or very high electrode counts (e.g., increased density or number of electrodes per unit area). The substrate can be made from the class of materials known as semiconductors (e.g., silicon, gallium arsenide, germanium, silicon carbide, or the like).

FIG. 1 illustrates an example system 100 including an implantable medical device 110. The system 100 can include the implantable medical device 110, a housing 120, an interior chamber (not shown) in the housing 120, an opening 140, a circuit 150, a feedthrough 160 or feedthrough 161 or both, a substrate 170 or substrate 171 or both, and a first electronic component 180. The implantable medical device 110 can have a housing 120. The housing 120 can be manufactured from a biocompatible material (e.g., plastics or metals). The biocompatible material can be titanium or a titanium alloy. The housing 120 can be implanted subcutaneously or external to a body. The housing 120 can be configured to have (e.g., define) the interior chamber (not shown). The housing 120 can have portions that define an opening 140. The opening 140 can be a hole in the housing 120. The implantable medical device 110 can include more than one opening 140. The opening 140 can be located in positions other than that shown in FIG. 1.

The interior chamber (not shown) can contain (e.g., house, protect, or isolate) the circuit 150. The circuit 150 can be configured to perform various functions, such as sensing physiological signals, processing those physiological signals (e.g., determining a heart rate or a heart that is experiencing fibrillation), determining if a specified therapy needs to be applied in response to the sensed physiological signals, applying a specified therapy in response to the sensed physiological signals, or the like. More than one circuit 150 can be located within the interior chamber (not shown), and can be referred to as circuitry 150. The circuitry 150 can include a battery (not shown). The circuitry 150 can include a telemetry module (not shown) that facilitates either wired or wireless communication of information to external circuitry that is not located within the interior chamber. The information can include data that is representative of the various functions describe above (e.g., sensed physiological signals).

In an example, the feedthrough 160 can include a substrate 170. The substrate 170 can be coupled to the housing 120. The substrate 170 can be coupled to the housing 120 proximate to the opening 140. The substrate 170 can be hermetically coupled to the housing 120. The hermetical coupling of the substrate 170 and the housing 120 can include fabricating a seal between the substrate 170 and the housing 120 such that a bodily fluid (not shown), or other foreign material, is unable to pass from the exterior of the implantable medical device 110 (e.g., fluid in a chest cavity) to the interior of the implantable medical device 110 (e.g., the interior chamber). The passing of foreign material into the interior of the implantable medical device 110 can damage or destroy internal components of the implantable medical device 110, such as the circuitry 150.

Figure 3:
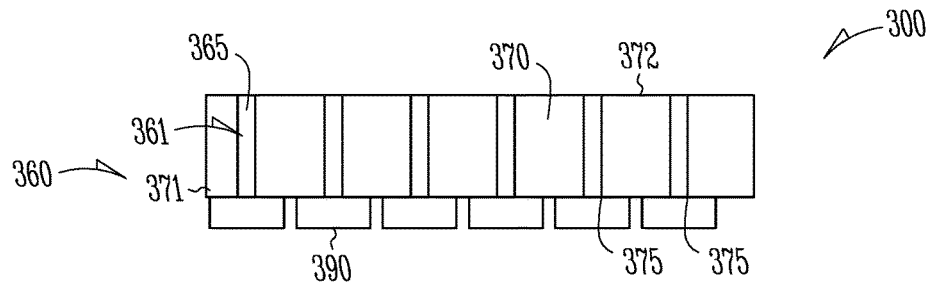
FIG. 3 illustrates an example system including a feedthrough for use with an implantable medical device.

In another example, an upper portion 190 of the implantable medical device 110 can be configured as a medical device header 191, which can be configured for example to receive a medical device lead. The header 191 can, for example, be formed of a polymer which can for example be overmolded over electrical components. In this scenario, a feedthrough 161 can connect circuitry 150 inside the housing 120 with electrical components (not shown) in the header 191. The feedthrough 161 can include a substrate 171 and electrical vias through the substrate 171 (as shown in FIG. 3, for example) that provide an electrical connection between components in the header 191 and the circuitry 150. The substrate 171 can be hermetically bonded to the housing 120. The substrate 171 can optionally be overmolded into the header 191.

As will be discussed further herein, the feedthrough 160 can be configured to allow one or more electrically-isolated electrical connections (e.g., communication pathways) to be established between the circuitry 150 contained within the interior chamber, and one or more electronic components (e.g., first electronic component 180) located outside of the interior chamber of the implantable medical device 110. The first electronic component 180 can be a wire, a lead, a sensor, active circuitry, passive components, a defibrillator, a pacing stimulator, other type of stimulators, an electrode, a spike electrode, or the like. If more than one electronic component (e.g., first electronic component 180) is used, the electronic components can be considered a plurality of electronic components. The plurality of electronic components (not shown) can be located outside of the interior chamber.

Figure 2:
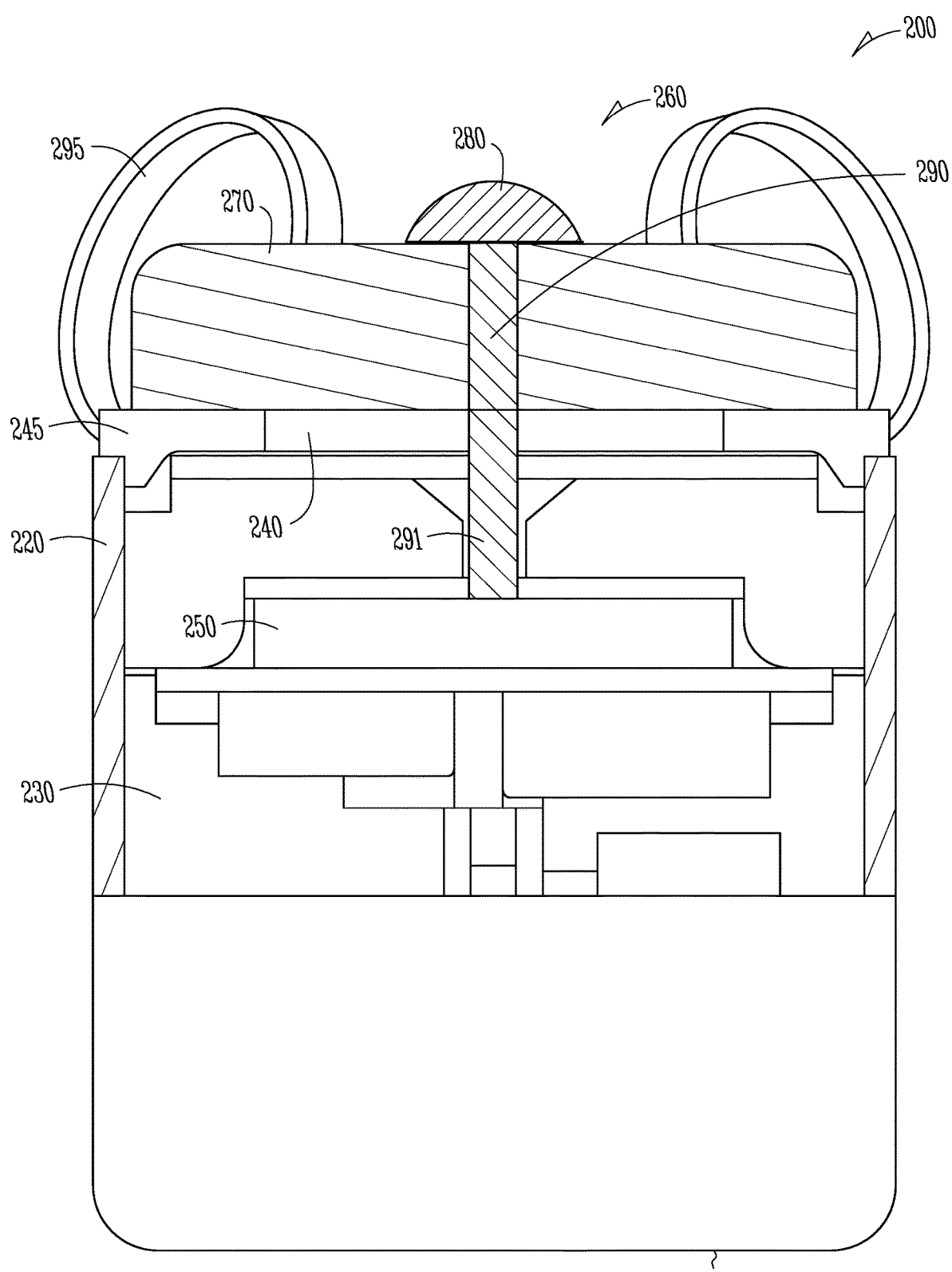
FIG. 2 illustrates another example system that includes an implantable medical device.

FIG. 2 illustrates another example system 200 that includes an implantable medical device 210. The implantable medical device 210 can include a housing 220, an interior chamber 230, an opening 240, circuitry 250, a feedthrough 260, an electronic component 280, and one or more fixation members fixation member 295. The one or more fixation members 295 can, for example, include tines, struts, or hooks, or an expandable structure such as a stent. The feedthrough 260 can include a substrate 270 and one or more conductors 290 (e.g. electrical vias) that extend through the substrate. An additional conductor 291 can connect the conductor 290 to circuit 250. In another example, the circuit 250 can be directly connected to the conductor 290. The housing 220 can be made of a biocompatible material such as titanium. The housing 220 can be configured to have an interior chamber 230. The interior chamber 230 can contain circuitry 250. The housing 220 can have portions that define an opening 240. The housing 220 can have an end portion 245. The opening 240 in the housing 220 can be located at the end portion 245 of the housing 240. The opening 240 can, for example, be a hole in the housing 220 that is sized and shaped to accommodate bonding a circuit board (e.g., substrate 270) against an exterior surface of the housing as shown in FIG. 2. In another example, the substrate 270 can be placed inside the housing 220 over the opening 240, and bonded to an inside surface of the housing 220, to portions defining the opening 240, or both. The opening 240 can provide access to the interior chamber 230, such as for manufacturing and assembly of the implantable medical device 210. The circuitry 250 can be manufactured similarly to, function similarly to, and/or include the circuitry 150 (as shown in FIG. 1). One or more circuits (e.g., circuitry 250) can be located in the interior chamber 230.

The feedthrough 260 can be manufactured similarly to, function similarly to, and/or include the feedthrough 160 or feedthrough 190 (as shown in FIG. 1). The feedthrough 260 can be coupled to one or more conductors 291. The one or more conductors 291 can be electrically coupled with one or more vias (e.g., a plurality of vias) of the feedthrough 260. The one or more conductors 291 can establish one or more electrically-isolated electrical communication pathways (e.g., connections) between the circuitry 250 and the feedthrough 260 (or the one or more vias of the feedthrough 260). The feedthrough 260 can be coupled to an electronic component 280, which can, for example, be or include a stimulation electrode or a sensing electrode, or both. The feedthrough 260 can be coupled to one or more electronic components (not shown), as previously described with reference to the feedthrough 160 of FIG. 1.

The one or more fixation members 295 can be coupled to the housing 220. In some examples, the one or more fixation members 295 can be coupled to the feedthrough 260. The one or more fixation members 295 can be configured to penetrate (e.g., pierce) a bodily tissue and/or retain (e.g., fixation member onto, grasp, clasp, or the like) the bodily tissue. In some examples, the one or more fixation members 295 can be in electrical communication with the feedthrough 260. The electrical communication of the one or more fixation members 295 can establish an electrical communication pathway between the circuitry 250 and the one or more fixation members 295. The feedthrough 260 can provide an electrically-isolated electrical connection between the circuitry 250 and each of the one or more fixation members 295 and also between the electronic component 280 (or additional electronic components). The one or more fixation members 295 can be configured to function as electrodes, such as to sense physiological signals or to provide a specified therapy. The one or more fixation members 295 can be included in a plurality of electronic components (not shown) that are not in the interior chamber 230. The one or more fixation members 295 can be included in an array of sensors (not shown). The one or more fixation members 295 can be included in a plurality of stimulation electrodes (not shown). The implantable medical device 210 can include a control circuit (e.g., circuitry 250) that can be configured to selectively activate a subset of a plurality of electronic components (e.g., the one or more fixation members 295 and the electronic component 280). The subset of the plurality of electronic components can form a selectable sensor array or a selectable stimulation array.

FIG. 3 illustrates an example system including a feedthrough 360 for use with an implantable medical device 310. The feedthrough 360 can include a substrate 370. The substrate 370 can include a first substrate surface 371 and a second substrate surface 372. The first substrate surface 371 can face the inside of a housing (e.g., housing 220 of FIG. 2). The first substrate surface 371 can be located inside of a housing (not shown). The second substrate surface 372 can face toward the outside of a housing (not shown). The first substrate surface 371 or the second substrate surface 372 can be hermetically sealed against a housing (e.g., housing 220 of FIG. 2). The first substrate surface 371 or the second substrate surface 372 can be hermetically sealed against an outer surface of a housing (e.g., housing 220 of FIG. 2). The substrate 370 can include one or more substrate openings 375. The one or more substrate openings 375 can extend from the first substrate surface 371 to the second substrate surface 372. The substrate 370 can be configured for juxtaposition against a biological fluid (e.g. the substrate 370 is made of a biocompatible material). The substrate 370 can be impervious to the biological fluid (not shown).

The feedthrough 360 can include a first via 361. The first via 361 can include a conductor 365 passing through the one or more substrate openings 375. The conductor 365 can be capable of transmitting electrical energy. The conductor 365 can electrically couple the first substrate surface 371 with the second substrate surface 372. A via (e.g., first via 361) can extend from the first substrate surface 371 to the second substrate surface 372. The feedthrough 360 can include a plurality of (e.g., include more than one) vias, wherein each of the plurality of vias are electrically-isolated from the other vias in the plurality of vias. The first via 361 can electrically couple (e.g., establish an electrical communication pathway or establish an electrical connection) a first electronic component (e.g., electronic component 280 in FIG. 2) with a circuit (e.g., circuitry 250 in FIG. 2). The vias (e.g., first via 361) can be hermetically coupled to the substrate 370 such that a biological fluid cannot pass through the one or more substrate openings 375 from the first substrate surface 371 to the second substrate surface 372.

The feedthrough 360 can include an electrode 390. The feedthrough can include one or more electrodes. The electrode 390 can be physically and electrically coupled with the first via 361. The electrode 390 can be located on the first substrate surface 371 and/or the second substrate surface 372. The electrode 390 can be configured to serve as an attachment point for other conductors (e.g., conductor 291 of FIG. 2). The electrode 390 can provide a suitable feature to allow for the interconnection of electronic components (e.g., first electronic component 180 of FIG. 1 or circuitry 250 of FIG. 2) with a via (e.g., first via 361). In an example, wherein the feedthrough 360 includes a plurality of vias, an electrode 390 can be coupled to each via of the plurality of vias, while remaining electrically-isolated from the other electrodes and vias. An electrode 390 can be coupled to each end of each of the vias of the plurality of vias.

The electrode 390 can also be referred to as an interconnect. The electrode can also be referred to as an electronic component. While an interconnect can also be considered an electronic component, that may not necessarily always be true. In an example, the feedthrough 360 can include an interconnect (e.g., electrode 390) that is coupled to a conductor (e.g., conductor 365) and the second substrate surface 372. The feedthrough 360 can include an electronic component (e.g., a MEMS device as discussed with reference to FIG. 4 or a lead) that is coupled to the conductor 365 and the first substrate surface 371. The interconnect can be in electrical communication with the electronic component (not shown), such as by virtue of both the interconnect and the electronic component being coupled to the conductor. In another example, an electrode 390 can be coupled to the first substrate surface 371 and an electrode 390 can be coupled to the second substrate surface 371. The electrodes can be in electrical communication by both being coupled to a conductor (e.g., conductor 365) that electrically couples the first substrate surface 371 and the second substrate surface 372. In this example, the electrode coupled to the first substrate surface 371 is an electronic component, and the electrode coupled to the second substrate surface 372 is an interconnect, yet the interconnect and the electronic component are both an electrode (e.g., the same feature, but located on opposite sides of the substrate 370).

The feedthrough 360 can include one or more interconnects. The feedthrough 360 can include one or more electronic components (not shown). Each of the one or more interconnects can be electrically coupled to a respective electronic component of the one or more electronic components, such as through the use of a plurality of vias, with each via extending between each of the electronic components and interconnects. The interconnects can be electrically coupled with circuitry (e.g., circuitry 150 of FIG. 1).

Figure 4:
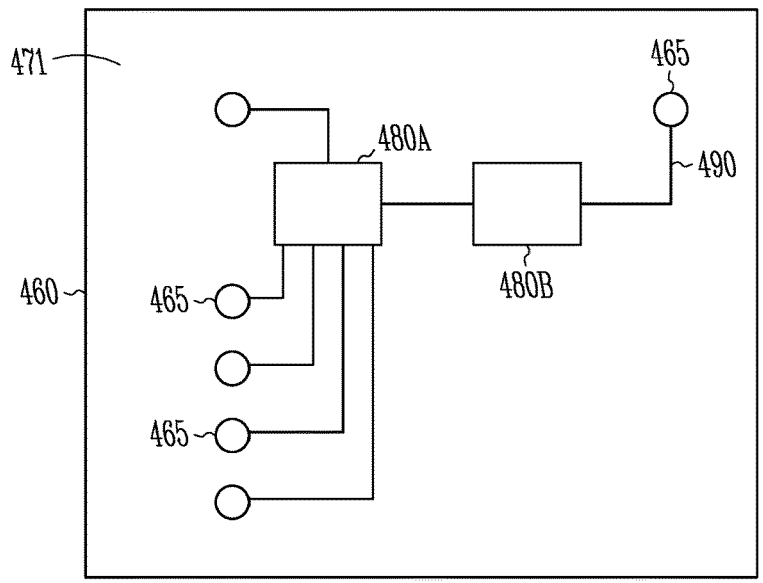
FIG. 4 illustrates an example system including another feedthrough for use with an implantable medical device.

FIG. 4 illustrates an example system including another feedthrough 460 for use with an implantable medical device. The feedthrough 460 can include a first substrate surface 471, one or more vias 465, a first electronic component 480A, a second electronic component 480B, and one or more traces 490. The feedthrough 460 can include a plurality of vias 465 that are configured to provide an electrical connection from the first substrate surface 471 to a second substrate surface (not shown). The traces 490 can be configured to provide an electrically-isolated electrical communication pathway between the plurality of vias 465 and the first electronic component 480A, the second electronic component 480B, to another via of the plurality of vias, or a combination thereof.

The first or second electronic component 480A, 480B can include a micro-electromechanical system ("MEMS"). The MEMS can include a pressure sensor. The first or second electronic component 480A, 480B can be integrated onto the substrate. The first or second electronic component 480A, 480B can be fabricated using known integrated circuit techniques. The first or second electronic component 480A, 480B can be located inside of an interior chamber (e.g., interior chamber 130 of FIG. 1) of an implantable medical device (not shown). The first or second electronic component 480A, 480B can be located outside of an interior chamber (e.g., interior chamber 130 of FIG. 1) of an implantable medical device. The first or second electronic component 480A, 480B can include, or be included in, a plurality of electrodes (not shown). The plurality of electrodes can be in electrical communication with circuitry (e.g., circuitry 250 of FIG. 2), wherein the circuitry is configured to activate (e.g., energize and receive signals from) a selected subset of the plurality of electrodes. The first or second electronic components 480A, 480B can be included in, or referred to as, plurality of electronic components. The plurality of electronic components can include an array of sensors. The plurality of electronic components can include a plurality of stimulation electrodes (not shown).

As will be discussed with reference to FIG. 6, the first or second electronic component 480A, 480B can include a spike electrode (not shown). The spike electrode can be configured to penetrate bodily tissue, such as by being shaped like a needle, pin, spike, or the like. The spike electrode can have one or more isolated sub-electrodes. The sub-electrodes can be electrically isolated. The spike electrode can include an array of sensors. The spike electrode can include a plurality of stimulation electrodes. The array of sensors or the plurality of stimulation electrodes can be considered a subset of the plurality of electronic components. The subset of the plurality of electronic components can be in communication with a control circuit that is configured to selectively activate the subset of the plurality of electronic components.

Figure 5:
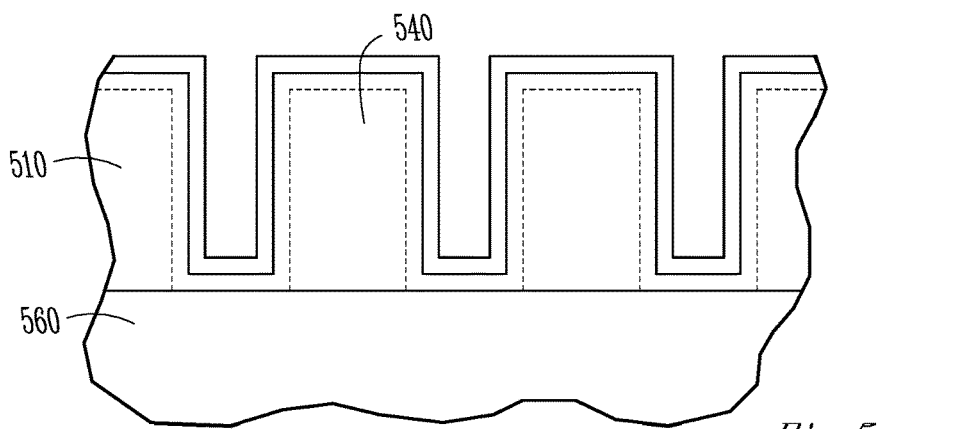
FIG. 5 illustrates an example system including a feedthrough with surface features that increase the surface area of the feedthrough.

FIG. 5 illustrates an example system 500 including a feedthrough 560 with surface features 540 that increase the surface area of the feedthrough 560. The surface features 540 can include one or more trenches (e.g., a well, trough, or the like). The addition of one or more trenches can increase the surface area of the feedthrough 560. The surface features 540 can be fabricated by coating the substrate 510 with a material that increases the surface area of the feedthrough 560. The coating material can be a high surface area density coating. The coating can be applied to a first or a second substrate surface (e.g., first or second substrate surface 371, 372 of FIG. 3). Increasing the surface area of the feedthrough 560 can result in more of the feedthrough 560 (e.g., first or second substrate surface 371, 372 of FIG. 3) being in contact with the bodily or biological fluids of a patient. Although the shape of the one or more trenches shown in FIG. 5 are rectangular in shape, it is now appreciated that the shape of the one or more trenches can have other polygon shapes, mimic sinusoidal waves, or have other irregular shapes.

Figure 6A:
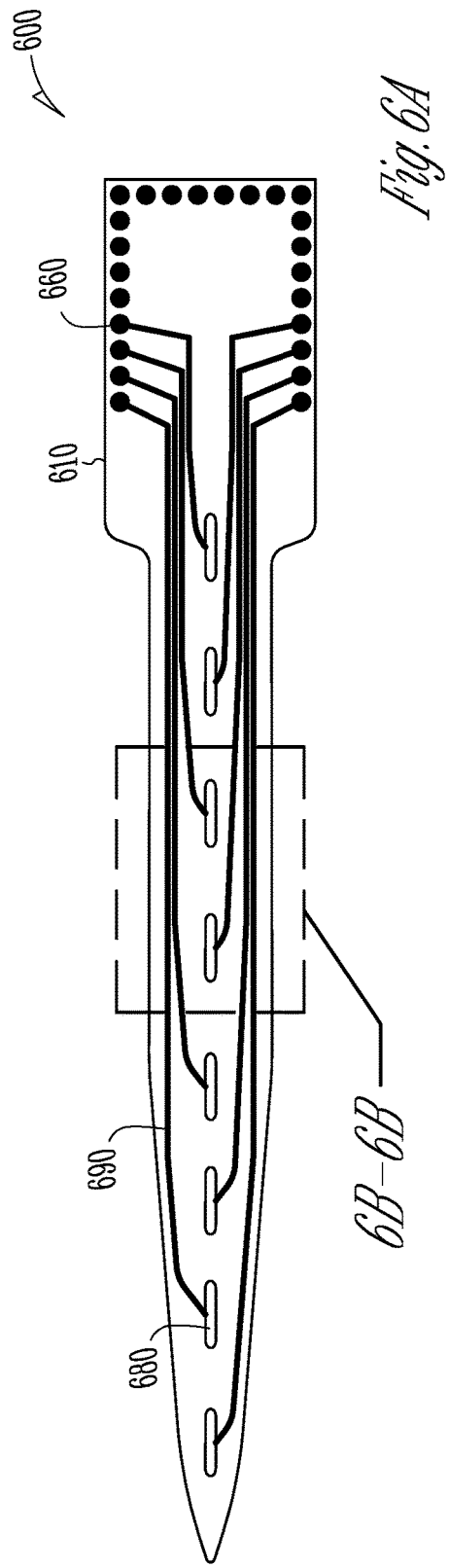
FIG. 6A illustrates an example system including a spike electrode.

FIG. 6A illustrates an example system 600 including a spike electrode 610. The system 600 can include the spike electrode 610, one or more electrically-isolated vias 660, one or more interconnects 665, a substrate 670, one or more electronic components 680, and one or more leads 690. The system 600 can include a plurality of electronic components (not shown). The system 600 can include a substrate 670 that includes a feedthrough (as previously discussed herein) and a spike electrode 610. The spike electrode 610 can include the elements, features, and functions of the feedthroughs as previously discussed with reference to FIGS. 1 through 5. The one or more vias 660 can be configured and function similar to, or the same as, the vias described with reference to FIGS. 1 through 4. The spike electrode 610 can be configured to penetrate bodily tissue, such as by being shaped like a needle, pin, spike, or the like.

The spike electrode 610 can have one or more isolated sub-electrodes (e.g., one or more electronic components 680). The spike electrode 610 can have a plurality of isolated sub-electrodes. The sub-electrodes can be electrically isolated from each other. The one or more electronic components 680 can include an array of sensors. The one or more electronic components 680 can include a plurality of stimulation electrodes. The array of sensors or the plurality of stimulation electrodes can be considered a subset of the plurality of (or one or more) electronic components. The subset of the plurality of electronic components can be in communication with a control circuit that is configured to selectively activate the subset of the plurality of electronic components.

The leads 690 can provide an electrical connection between the one or more electronic components 680 and the one or more interconnects 665. The leads 690 can provide an electrical connection between the one or more electronic components 680 and the one or more electrically-isolated vias 660. The leads 690 can provide an electrical connection between an individual electronic component of the one or more electronic components 680 and another electronic component of the one or more electronic components 680. The interconnects can be electrodes, pads, or the like that can be configured as coupling points for the electrical connection of the spike electrode 610 with other electronics (e.g., circuitry 150 of FIG. 1).

Figure 6B:
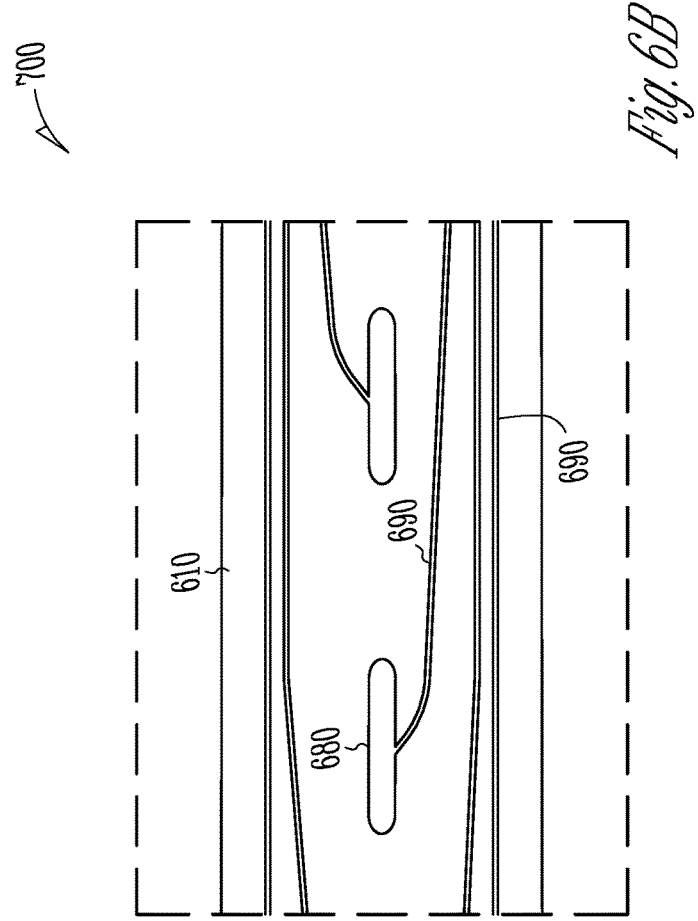
FIG. 6B illustrates a detailed view of the example system of FIG. 6A.

FIG. 6B illustrates a detailed view of the example system 600 of FIG. 6A. The system 600 can include a substrate 670, one or more electronic components 680, and one or more leads 690. FIG. 6B shows in greater detail the electrically isolated nature of the leads 690 and electronic component 680 that are located on the substrate 670.

Figure 7:
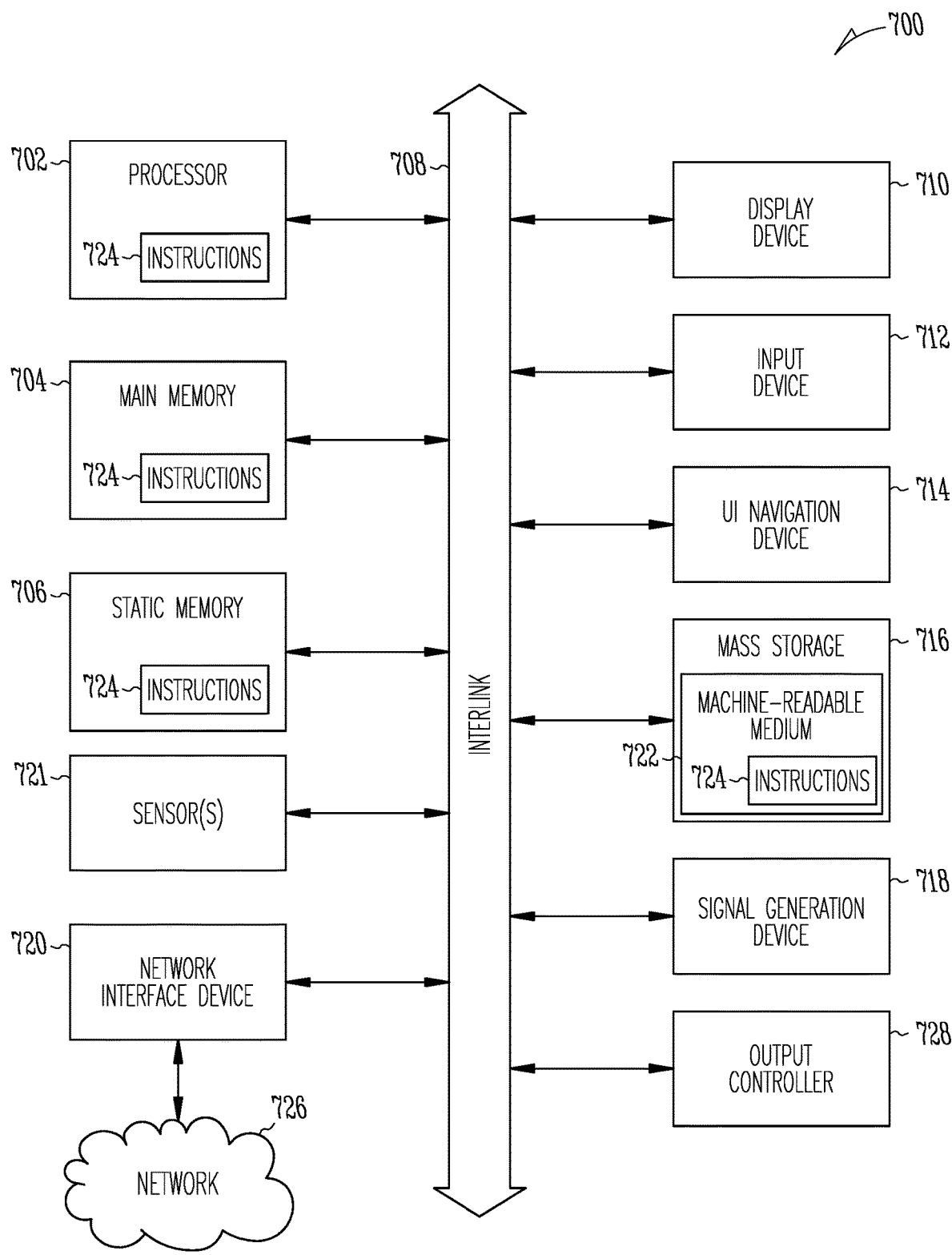
FIG. 7 illustrates a block diagram of an example machine into which a feedthrough may be integrated and upon which any one or more of the techniques discussed herein may perform.

FIG. 7 illustrates a block diagram of an example machine into which a feedthrough (e.g., feedthrough 360 of FIG. 3) may be integrated and upon which any one or more of the techniques (e.g., methodologies) discussed herein may perform. Portions of this description may apply to the computing framework of various portions of the implantable medical device, such as implantable medical device 110 of FIG. 1 or the external system, or an implantable device operating as part of a system. In alternative embodiments, the machine 700 may operate as a standalone device or may be connected (e.g., networked) to other machines. For example, in a networked deployment, the machine 700 may operate in the capacity of a server machine, a client machine, or both in server-client network environments. In some examples, portions of the machine such as stimulation therapy electrodes coupled to an output controller 728, may be part of or coupled to an implantable device, and other portions, such as a touchscreen input device, display device, or physical ports may be part of an external (non-implanted) system.

In an example, the machine 700 may act as a peer machine in peer-to-peer (P2P) (or other distributed) network environment. The machine 700 may be or include a special purpose implantable or wearable device, personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit (e.g., circuit 150) of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a piezoelectric buzzer), a network interface device 720 such as a MICS or Bluetooth radio, and one or more sensors 721, such as an electrode capable of detecting cardiac signals (e.g., cardiac activation or depolarization), respiration, an acoustic sensor configured to detect heart sounds, or other physiologic signals, a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Figure 8:
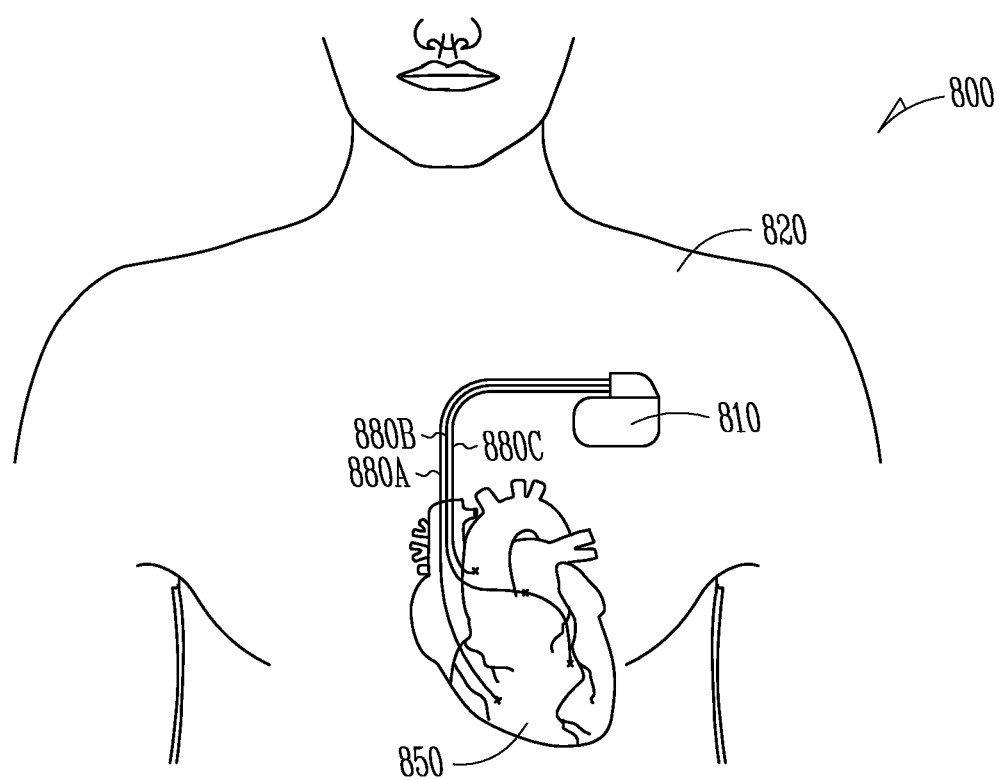
FIG. 8 illustrates an example system of an implantable medical device located within a patient.

FIG. 8 illustrates an example system 800 of an implantable medical device 810 located within a patient 820. The system 800 can include the implantable medical device 810; and one or more electronic components 880A, 880B, 880C (such as pacing or defibrillation leads) that can be placed at a desired location, such as on or in a heart 850. As previously discussed herein, the implantable medical device 810 can be located within a patient 820. In an example, the implantable medical device 810 can be a pacemaker that can be implanted in the patient 820 and provide stimulation (e.g., pacing or defibrillation) to the heart 850. In another example, the implantable medical device 810 can be a neurostimulator that can provide stimulation to a nerve or one or more regions of a brain of the patient 820. Implantable medical devices range in size and function, and can be utilized in numerous other portions of the body.

Figure 9:
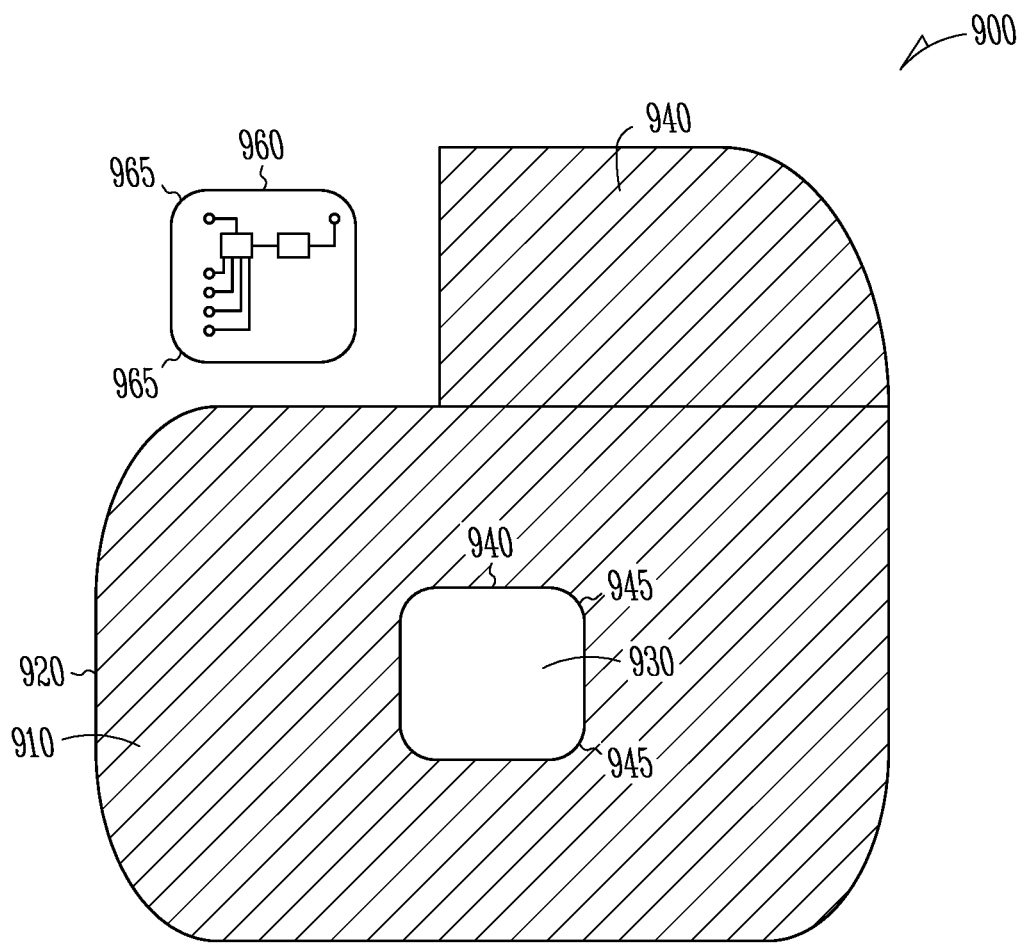
FIG. 9 illustrates an example system including a feedthrough for use with an implantable medical device.

FIG. 9 illustrates an example system 900 including a feedthrough 960 for use with an implantable medical device 910. The system 900 can include an implantable medical device 910, a housing 920, an internal chamber 930, an opening 940, a first set of rounded corners 945, a feedthrough 960, a second set of rounded corners 965, and a substrate 970. The opening 940 in the housing 920 can include a first set of rounded corners 945. The substrate 970 can include a second set of rounded corners 965. The first set of rounded corners 945 can match the second set of rounded corners 965 to facilitate hermetically sealing the feedthrough 960 to the housing 920 of the implantable medical device 910.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. An implantable medical device, comprising:
   a housing portion defining an interior chamber, the housing having portions defining an opening;
   a circuit in the interior chamber;
   a first electronic component that is not in the interior chamber;
   an implantable medical device feedthrough comprising a substrate hermetically coupled to the housing proximate the opening, wherein the substrate is formed from a semiconductor material, the substrate including:
      a first substrate surface configured for juxtaposition against a biological fluid; and
      a first via extending through the substrate, the first via electrically coupling the first electronic component at the first surface of the substrate to the circuit in the interior chamber,
      a set of rounded corners to facilitate hermitically sealing the implantable medical device feedthrough to the housing.

2. The implantable medical device of claim 1, wherein the implantable medical device includes a micro-electromechanical system ("MEMS") that includes the first electronic component.

3. The implantable medical device of claim 2, wherein the micro-electromechanical system includes a pressure sensor.

4. The implantable medical device of claim 1, wherein the first electronic component is integrated onto the substrate.

5. The implantable medical device of claim 1, wherein a first surface of the substrate is inside the housing and a second surface of the substrate faces outside of the housing, the via providing an electrical feedthrough that extends from the first surface to the second surface, and the first surface or the second surface is hermetically sealed against the housing.

6. The implantable medical device of claim 5, wherein the first surface of the substrate is hermetically sealed against an outer surface of the housing.

7. The implantable medical device of claim 1, further comprising:
   a plurality of electrodes that includes the first electronic component; and
   circuitry that is configured to activate a selected subset of the plurality of electrodes.

8. The implantable medical device of claim 1, wherein the first electronic component is a spike electrode and the spike electrode has one or more isolated sub-electrodes.

9. An implantable medical device comprising:
   a housing defining an interior chamber;
   one or more circuits in the interior chamber;
   a plurality of electronic components that are not in the interior chamber;
   an implantable medical device feedthrough comprising a substrate that is configured to hermetically couple with the housing, wherein the substrate is formed from a semiconductor material, the substrate including:
      a first substrate surface configured for juxtaposition against a biological fluid; and
      a plurality of vias extending through the substrate, each of the plurality of electronic components at the first surface of the substrate is electrically coupled to at least one of the one or more circuits in the interior chamber through at least one of the one or more vias,
      a set of rounded corners to facilitate hermitically sealing the implantable medical device feedthrough to the housing.

10. The implantable medical device of claim 9, wherein the plurality of electronic components includes an array of sensors.

11. The implantable medical device of claim 9, the plurality of electronic components includes a plurality of stimulation electrodes.

12. The implantable medical device of claim 9, wherein the implantable medical device includes a control circuit that is configured to selectively activate a subset of the plurality of electronic components, the subset forming a selectable sensor array or a selectable stimulation array.

13. The implantable medical device of claim 9, wherein the plurality of electronic components form a spike electrode and the spike electrode is configured to penetrate bodily tissue.

14. The implantable medical device of claim 1, comprising a fixation member configured to affix the implantable medical device to a bodily tissue of a patient.

15. The implantable medical device of claim 14, wherein the fixation member is configured to position the first electronic component at the first surface of the substrate at a particular location in or around a heart of the patient.

16. The implantable medical device of claim 15, wherein the fixation member comprises an electrode electrically coupled to the first via, and
   wherein the first electronic component includes the fixation member.

17. The implantable medical device of claim 15, wherein the fixation member is coupled to the substrate.

18. The implantable medical device of claim 15, wherein the housing portion of the implantable medical device is elongate, and
   wherein the fixation member and the first electronic component are at a first end of the implantable medical device.

* * * * *